United States Patent [19]

Canducci

[11] Patent Number: 4,961,423

[45] Date of Patent: Oct. 9, 1990

[54] RATE ADAPTIVE MYOELECTRIC PACER

[75] Inventor: Gian C. Canducci, Bologna, Italy

[73] Assignee: Medtronic, Inc., Minneapolis, Minn.

[21] Appl. No.: 223,969

[22] Filed: Jul. 15, 1988

[51] Int. Cl.$^5$ ............................................ A61N 1/365
[52] U.S. Cl. ............................................ 128/419 PG
[58] Field of Search ................ 128/419 PG, 671, 721

[56] References Cited

U.S. PATENT DOCUMENTS

| | | | |
|---|---|---|---|
| 4,379,460 | 4/1983 | Judell | 128/671 |
| 4,694,830 | 9/1987 | Lekholm | 128/419 PG |
| 4,702,253 | 10/1987 | Nappholz et al. | 128/419 PG |
| 4,757,815 | 7/1988 | Strandberg et al. | 128/419 PG |
| 4,781,201 | 11/1988 | Wright et al. | 128/671 |

FOREIGN PATENT DOCUMENTS 0226164 6/1987 European Pat. Off. .
0294949 12/1988 European Pat. Off. .

OTHER PUBLICATIONS

Article, "Variation of Cardiac Output Relative to Pacemaker Rate", by W. A. Getzel et al., *Proceedings of the 32nd Conference on Engineering in Medicine and Biology*, p. 123, 1979.
Article, "Variation of Cardiac Pacemaker Rate Relative to Respiration", by Getzel et al., *IEEE Transactions on Biomedical Engineering*, vol. BME-26, No. 9, p. 526, Sept., 1979.

*Primary Examiner*—Lee S. Cohen
*Assistant Examiner*—S. Getzow
*Attorney, Agent, or Firm*—Reed A. Duthler; Joseph F. Breimayer

[57] ABSTRACT

A rate responsive pacer is disclosed which alters the pacer's escape interval in response to the patient's metabolic demand. Metabolic demand is determined from the patient's respiration rate which is extracted from spontaneous muscle signals.

3 Claims, 4 Drawing Sheets

RATE ADAPTIVE MYOELECTRIC PACER

BACKGROUND OF THE INVENTION

1Field of the Invention

This invention relates to cardiac pacemakers and more particularly to rate responsive pacers which alter the pacing rate based on the patient's metabolic demand.

2. Description of the Prior Art

Recently rate responsive pacemakers have been introduced. These devices adapt the escape interval or pacing rate of the pacer to the metabolic demands of the patient. A variety of sensors and approaches have been employed to estimate metabolic demand including the measurement of blood oxygen saturation; blood pH; central core temperature; blood pressure and its derivatives as well as cardiac stroke volume.

One especially promising technique to estimate metabolic demand involves the measurement of the patient's breathing rate and the computation of the mass flow rate of air into (and out of) the patient's lungs. This latter quantity is called the minute ventilation.

The use of impedance plethysmography to generate this type of information is known from U.S. Pat. No. 4,596,251 to Plicchi and Canducci. This prior art pacer derives the respiration rate through a thoracic impedance measurement using an auxillary lead.

Other investigators have proposed other sensor techniques and locations. Funke reported on the use of a microphone to monitor intrapleural or intrathoracic pressure in "Ein Herzschrittmacher mit Belastungsabhangiger Frequenzregulation" published in 1975 in BioMedische Tecknik. In this article Funke also suggested, and rejected, a system based on the detection of electrical activity of the diaphragm or the intercostal musculature.

More recently, Cunningham et al have demonstrated the electronic integration of the diaphragm electromyogram to generate a control signal proportional to respiratory minute volume for use as the controlling physiological input for a pacemaker; see "Variation of Cardiac Pacemaker Rate Relative to Respiration", IEEE, 1979.

Other methods of deriving a respiratory signal have been proposed more recently including the sensing of amplitude variations of the heart action signal as seen from EPO patent application No. 0 226 164 published June 24, 1987. It has also been proposed to extract an aspiration signal from respiration modulation of the impedance of the vascular bed as shown in U.S. Pat. No. 4,702,253 to Nappholz. Or, such a signal may be derived from the pacing current and voltage in a pacer as shown in U.S. Pat. No. 4,694,830 to Leckholm.

In each of these prior art devices, a respiration dependent signal is extracted and used to drive the pacing rate. The present invention is like the prior art in this regard.

SUMMARY OF THE INVENTION

However, in contrast to these prior art teachings, the present invention extracts the respiration signal from a different source though the use of a different technique. In a preferred embodiment of the invention, the device employs an electromyogram sensor (EMG) in connection with an electrocardiogram (ECG) sensor to derive a control signal which reflects the patient's respiration. These two myoelectric sensors are used to generate a control signal which is used to alter the pacing rate.

The first sensor is called the EMG sensor. This sensor comprises an amplifier circuit which operates in the frequency domain and is configured to extract the potentials associated with the depolarization of muscle tissue.

The second sensor is called the ECG sensor, and it is similar to a conventional cardiac sense amplifier. The signal from the ECG sensor is used to interrupt EMG sensing so that the EMG signal is not corrupted by QRS signal components within the passband of the EMG sensor. Consequently the muscle signals are not monitored when the heart is being paced or is beating on its own. The time domain sampled EMG signal is "averaged" through the use of a half wave rectifier and a low pass filter centered at 0.3 Hz. This processing extracts the low frequency respiration induced modulation envelope of the muscle signal which is used as a control signal to alter the pacing rate of a conventional pulse generator circuit.

The signal processing circuitry of the present invention is coupled to the pacing lead system. The broad spectrum signal present on the lead is pass band filtered and amplified. Empirically determined corner frequencies of 150 Hz and 1500 Hz appear to best capture the desired 10-100 micro volt level muscle signal. Also present within this passband is an attenuated heartbeat signal which is removed by time domain filtering. This signal appears with the best signal to noise ratio when differentially sensed between the tip and can electrodes of the pacer system. However, the signal is also detectable between the ring and can and between the ring and tip on bipolar leads.

It is preferred to use conventional, unipolar tip electrodes and to share the EMG, ECG and pacing functions with the tip and can electrode pair. However, it may prove desirable to devote separate electrodes to the various functions.

The underlying physical processes exploited by the invention are not well characterized, but three separate mechanisms appear to contribute to the signal detected by the pacer of the present invention.

The musculature of the thorax includes both postural and motor units. These undergo depolarization and therefore generate electrical signals. The resultant electrical potentials generate electrical fields which may be detected by suitable circuitry. These myoelectric potentials may be amplitude modulated by the mechanical movements associated with breathing. This theory alone would suggest that the musculature may be modeled as a broad spectrum noise source which is amplitude modulated by respiration. However, empirical evidence suggests that the detection of the modulation envelope is enhanced at certain center frequencies which is not consistent with this simple theory.

Another contribution to the detected signal may result from the mechanical movement or displacement of the tip electrode in the heart and the pacer can on the chest. The measurement of myoelectric potentials depends strongly on the orientation of the electrode system, and movement of the lead system by respiration may contribute to the signal.

A third component may be the myoelectric contribution of the diaphragm muscle itself.

Research with voluntary motor unit muscle groups demonstrate that increasing workloads results in increasing firing rate of the fibers making up the muscle group. This frequency shift is characterized by a shift in the spectral peak in the power spectrum along with a concomitant shift in the harmonics. It may be that the act of respiration shifts power into relatively narrow pass bands in the frequency domain due to the characteristics of the diaphragm itself.

DESCRIPTION OF THE PREFERRED EMBODIMENT

Figure 1:
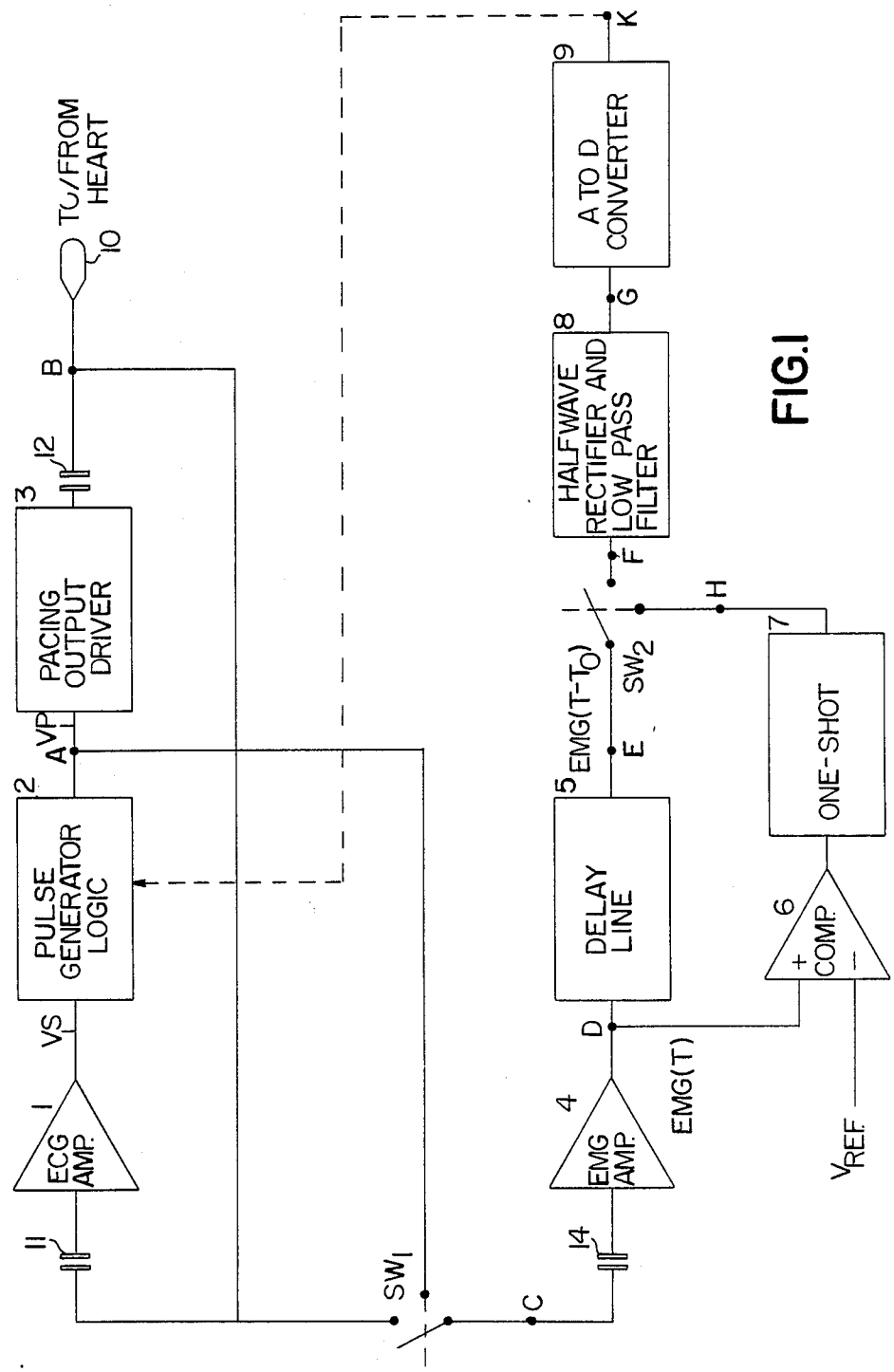
FIG. 1 is a system level block diagram of the circuitry of the invention.

The respiration controlled pacemaker is shown in a system level block diagram of FIG. 1. The figure includes several pacemaker structures well known in this art. These structures include the ECG or sense amplifier 1 which detects cardiac depolarizations, the pacing output driver 3 which stimulates the heart and the V—V escape interval timer circuit and associated pulse generator logic 2. The additional circuitry shown in FIG. 1 is also well known, and it is the combination of these elements and their interaction which comprises the apparatus for carrying out the present invention.

The circuitry shown in FIG. 1 is preferrably coupled to the heart via a conventional ventricular lead system connected to connector block terminal 10. Electrical signals generated by the heart are transferred to the ECG or sense amplifier via a coupling capacitor 11, while electrical stimuli generated by the output driver 3 are supplied to the heart via output capacitor 12.

In operation, a ventricular sense event (VS) signal is generated by the ECG amplifier 1 in response to a heartbeat. This signal is communicated to the timer logic within circuit 2. The pulse generator logic 2 includes a V to V escape interval timer which is resynchronized by each of these detected ventricular sense events in a known manner.

If no naturally occurring ventricular depolarization occurs within the V—V escape interval of the pacer, a ventricular pace signal (VP) will be issued by the timer circuit and coupled to the pacing output driver circuit. This signal, present at A, will result in the generation of an output pulse from circuit 3 which will discharge output capacitor 12 to stimulate the heart. An example of circuitry suitable for implementing this portion of the pacer can be found in U.S. Pat. No. 4,596,251 which is incorporated by reference.

As described in the summary, the occurrence of a ventricular stimulus interrupts the monitoring of the muscle signals present at the input of the EMG circuitry 4. This function is achieved in the illustrative embodiment by using the ventricular pace event signal generated by timer logic 2 at point A to open switch element SW1. This switch element interrupts signals present on the lead at B from coupling through capacitor 14 to the EMG amplifier 4.

Figure 2:
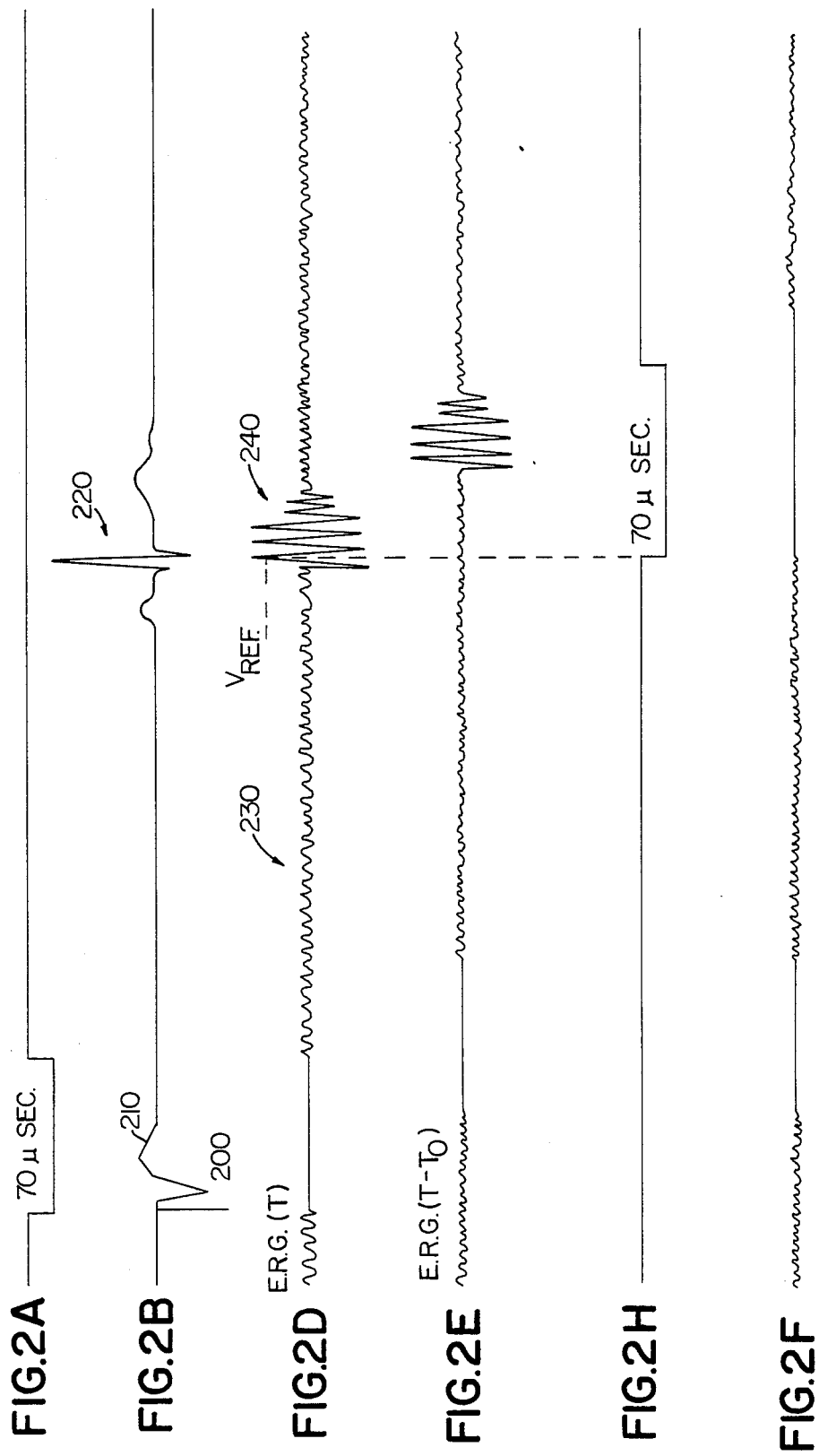
FIG. 2 is a timing diagram depicting the operation of the signal processing circuitry of the invention.

As shown in FIG. 1, this signal is applied to switch SW1 for approximately 70 ms to isolate the EMG amplifier 4 from the lead system 10 during the delivery of a ventricular stimulus (shown as 200 on FIG. 2) and for the duration of the resulting stimulated R wave (shown as 220 on FIG. 2).

However, during the interpulse interval 230, SW1 remains closed connecting the EMG amplifier 4 to the lead system through a coupling capacitor 14. During this time the EMG amplifier responds to the myoelectric signals. To adequately respond to these signals, the EMG amplifier should have a gain of approximately 2500 and should exhibit a maximally flat bandpass response between 300 to 700 Hz.

The representative waveforms shown on FIG. 2 as tracing D show the response of the EMG amplifier to the modulated muscle noise and later in the tracing to a spontaneous R-wave 220. It is clear from tracing D that the R wave signal generated by the heart at 220 has a significant amount of energy within the passband of the EMG amplifier 4 as shown at 240. The delay line 5, comparator 6 and one/shot 7 cooperate with switch SW2 to remove this heart noise by time domain filtering. The result of the functioning of these elements is shown in tracings E, H, F.

In operation, the magnitude of EMG signal at D is compared to a threshold reference by comparator 6 shown in FIG. 1. The high amplitude value of R-wave noise in the passband triggers the comparator which in turn initiates a 70 ms one/shot 7 which opens switch SW2 as shown in tracing H of FIG. 2. This sequence of operation results in the tracing D of FIG. 2 which shows that the switch SW1 remains open for a sufficiently long period of time to permit the EMG signal due to the R-wave to subside.

Tracing E shows the operation of the 10 ms signal delay provided by the delay line 5. As seen on FIG. 2, the delay time stores a historical sample of the EMG waveform. This delay is long enough to permit the R-wave exclusion circuitry to open switch 2 so that the rectifying and low pass filtering circuit 8 does not receive and average any signal components due to the R-wave as shown by tracing F on FIG. 2.

The R wave exclusion system described additionally avoids the sensing of myopotentials due to large scale movement of chest because such myopotentials would also exceed the threshold of comparator 6.

Thus, in operation, the pacemaker's endocardial lead system is coupled to am EMG amplifier which responds to the relatively high frequency respiration modulated muscle noise to generate a mypotential signal. This myopotential signal is subjected to low frequency filtering to extract the amplitude modulation envelope from the myopotential signal due to respiration. The modulation envelope extracted is presented to an analog to digital converter 9 which generates a digital word indicative of the respiration signal. This word is interpreted as rate information by the V—V timer logic circuit which adapts the escape interval portional to the magnitude of the respiration signal. The sampling time of the myopotential signal is interrupted in the presence of noise above a threshold and is interrupted by the sensing and pacing of R waves.

Figure 3:
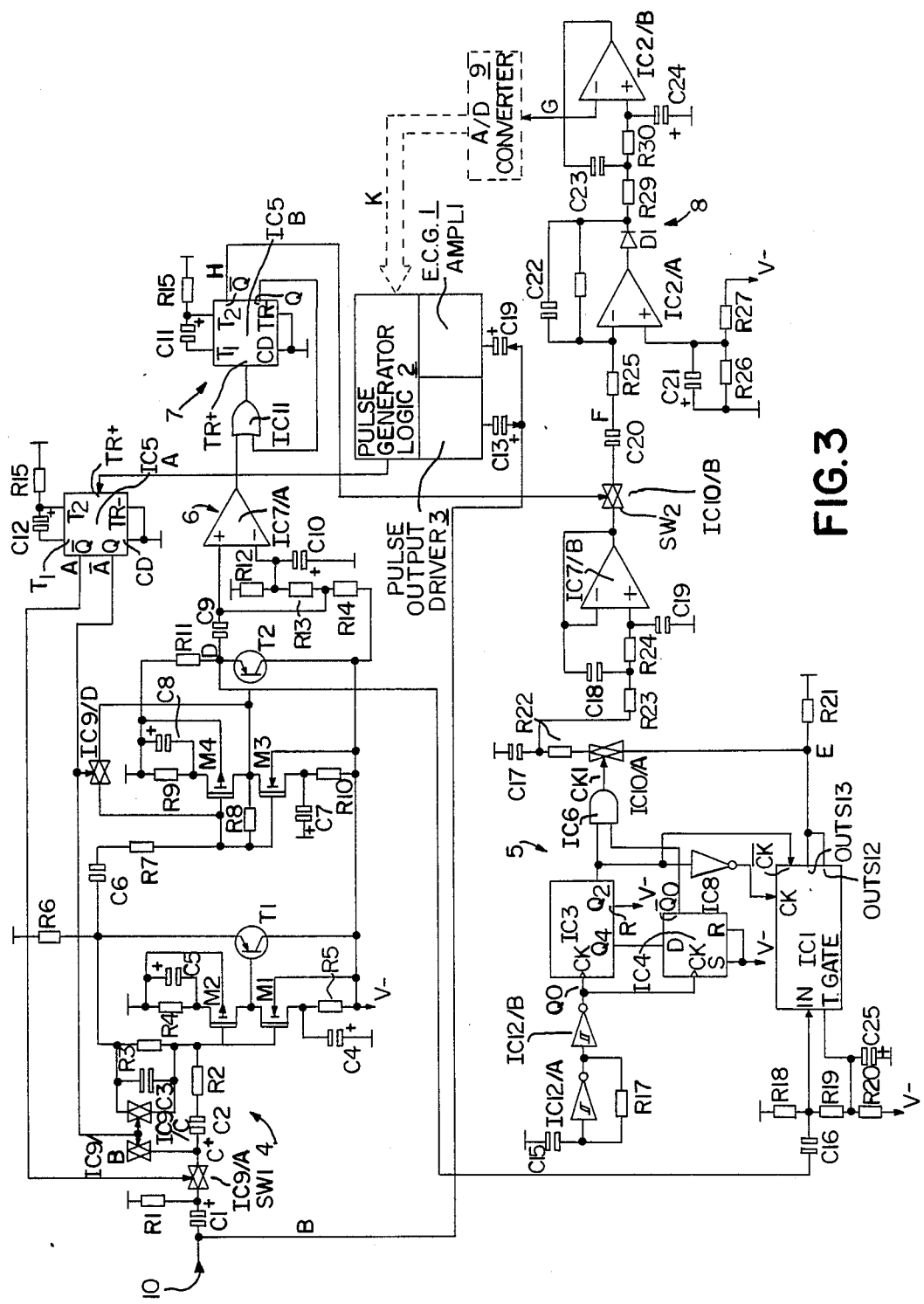
FIG. 3 is a schematic diagram setting forth an illustrative circuit for practicing the invention.

Turning to FIG. 3, there is shown a schematic diagram of a circuit for carrying out the invention.

Like numbers refer to the same structures throughout the figures of the drawing.

The system level elements 1, 2 and 3 are integrated into a proprietary integrated circuit. The functioning of these prior art elements are well known to those skilled in the art, and many equivalent and interchangeable circuits for performing the system level function are available. The remaining components and their values are set forth in the following table.

RESISTORS

| | | | |
|---|---|---|---|
| 1 | 330 | k ohm | 5% |
| 2 | 33 | k ohm | 5% |
| 3 | 2 | M ohm | 5% |
| 4 | 510 | k ohm | 5% |
| 5 | 510 | k ohm | 5% |
| 6 | 2 | M ohm | 5% |
| 7 | 300 | k ohm | 5% |
| 8 | 20 | M ohm | 5% |
| 9 | 510 | k ohm | 5% |
| 10 | 510 | k ohm | 5% |
| 11 | 1 | M ohm | 5% |
| 12 | 2.7 | M ohm | 5% |
| 13 | 510 | k ohm | 5% |
| 14 | 3.9 | M ohm | 5% |
| 15 | 1.1 | M ohm | 5% |
| 16 | 1.1 | M ohm | 5% |
| 17 | 4.7 | k ohm | 5% |
| 18 | 2.4 | M ohm | 5% |
| 19 | 4.7 | M ohm | 5% |
| 20 | 510 | k ohm | 5% |
| 21 | 47 | k ohm | 5% |
| 22 | 39 | k ohm | 5% |
| 23 | 39 | k ohm | 5% |
| 24 | 39 | k ohm | 5% |
| 25 | 100 | k ohm | 5% |
| 26 | 100 | k ohm | 5% |
| 27 | 100 | k ohm | 5% |
| 28 | 220 | k ohm | 5% |
| 29 | 1.1 | M ohm | 5% |
| 30 | 1.1 | M ohm | 5% |

CAPACITORS

| | | | |
|---|---|---|---|
| 1 | 33 | nF | Tant. |
| 2 | 100 | nF | Tant. |
| 3 | 22 | pF | Chip |
| 4 | 100 | nF | Tant. |
| 5 | 100 | nF | Tant. |
| 6 | 3.3 | nF | Chip |
| 7 | 100 | nF | Tant. |
| 8 | 100 | nF | Tant. |
| 9 | 3.3 | nF | Chip |
| 10 | 100 | nF | Tant. |
| 11 | 68 | nF | Tant. |
| 12 | 68 | nF | Tant. |
| 13 | 4.7 | uF | Tant. |
| 14 | 330 | nF | Tant. |
| 15 | 1 | nF | Chip |
| 16 | 680 | pF | Chip |
| 17 | 4.7 | nF | Chip |
| 18 | 22 | nF | Chip |
| 19 | 220 | pF | Chip |
| 20 | 22 | nF | Chip |
| 21 | 100 | nF | Tant. |
| 22 | 47 | nF | Chip |
| 23 | 440 | nF | 2 Chip 220nF |
| 24 | 220 | nF | Tant. |
| 25 | 100 | nF | Tant. |

INTEGRATED CIRCUITS

| IC | 1 | TDA 1022 | DELAY LINE |
|---|---|---|---|
| IC | 2 | TL082 | OPERATIONAL AMPLITIFERS |
| IC | 3 | 4040 | BINARY COUNTER |
| IC | 4 | 4013 | FFD |
| IC | 5 | 4538 | DUAL MONOSTABLE |
| IC | 6 | 4081 | AND GATE |
| IC | 7 | 4575 | OPERATIONAL AMPLIFIER COMPARATOR |
| IC | 8 | 4069 | INVERTER |
| IC | 9 | 4066 | BILATERAL SWITCH |
| IC | 10 | 4066 | BILATERAL SWITCH |
| IC | 11 | 4071 | OR GATE |

-continued

INTEGRATED CIRCUITS

| IC | 12 | 40106 | SCHMITT TRIGGER |
|---|---|---|---|

TRANSISTORS

| T1, T2 | BCW 61 |
|---|---|
| M1, M2, M3, M4 | 4007x& |

DIODE

D1, 1N4148

In operation, elements 1, 2 and 3 are coupled to connector block 10 to form a ventricular demand pacer which provides a ventricular stimulus through output capacitor C12 if no ventricular depolarization is sensed by ECG or sense amplifier 1 through coupling capacitor C14 within the escape interval of the V—V timer of pulse generator logic 2. The escape interval of the V—V timer is set by a digital word K which is presented to the pulse generator logic 2 by an analog to digital converter 9.

Figure 4:
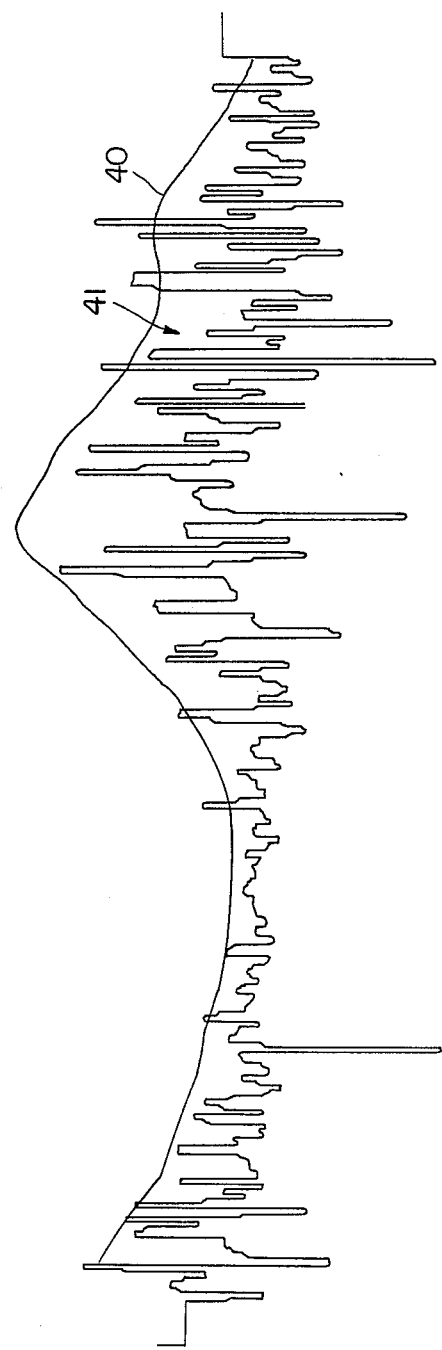
FIG. 4 is a waveform diagram showing the function of the rectification and low pass filtration on the EMG signal.

The signal which is converted to the word K by A/D converter 9 is shown in FIG. 4 as 40. This signal (G in FIG. 1) in the rectified and filtered EMG waveform (at point F in FIG. 1 and shown as 41 in FIG. 4).

At a more detailed level, the transistors M1, M2, M3, M4, T1 and T2 form a high gain (g=2500) bandpass amplifier for selective amplification of the low level myoelectric signals. These signals are coupled to the amplifier through SW1 which is controlled by the 70 ms one shot implemented with IC 5 section A.

The processed EMG signal is compared to a reference threshold by the comparator IC 7 section A. If the EMG signal exceeds the reference level, the EMG output is considered noise, and the comparator 17 C7 section A triggers the one shot IC 5 section B to generate the exclusion signal which controls switch SW2. While SW2 is open, the delayed electrogram signal present at the output of buffer IC 7/section B is excluded from the signal processing circuitry 8.

The signal processing circuitry at 8 preferably includes rectification and low pass amplification to generate a signal at G which reflects the patient's metabolic demand. Although the illustrative embodiment set pacing rate proportional to the patient's averaged respiration rate, it is contemplated that setting the rate proportional to minute ventilation may be desirable as well.

What is claimed is:

1. A cardiac pacemaker including pulse generator means for generating stimulating pulses and means for applying said stimulating pulses to the heart of a patient, comprising:

sensor means responsive to electrical activity of the heart and other muscles for producing a first EMG signal comprising myoelectric signals originating in the heart as well as myoelectric signals originating in other muscles;

signal processing means coupled to said sensor means for automatically identifying the occurrence of said myoelectric signals originating in the heart;

delay means coupled to said sensor means for providing a second EMG signal, delayed by a first predetermined time interval from said first EMG signal;

rate control means responsible to said second EMG signals for varying the rate of pulses generated by said pulse generator means as a function of said second EMG signal; and switch means for preventing said delayed EMG signal from affecting said rate control means for a second predetermined time interval following the automatic identification of one of said myoelectric signals originating in the heart, said second time interval being sufficient in duration to allow said one of said myoelectric signals originating in the heart, as delayed by said delay means, to subside prior to the expiration of said second time interval.

2. A pacemaker according to claim 1 wherein said means for identifying the occurrence of said myoelectric signals originating in the heart comprises means for measuring the amplitude of said first EMG signal.

3. A pacemaker according to claim 1 or claim 2 wherein said means for applying said stimulation pulses comprises a pacing electrode;

wherein said pacemaker further comprises a second electrode; and wherein said sensor means is coupled to said pacing electrode and said second electrode.

* * * * *